United States Patent

Grund et al.

[11] Patent Number: 5,756,807
[45] Date of Patent: May 26, 1998

[54] PREPARATION OF ALKYL CYANOACETATES

[75] Inventors: Clemens Grund, Mannheim; Martin Holderbaum, Ludwigshafen; Helmut Reichelt, Neustadt; Stefan Beckmann, Bad Dürkheim, all of Germany

[73] Assignee: BASF Aktiengesellschaft, Ludwigshafen, Germany

[21] Appl. No.: 734,271

[22] Filed: Oct. 21, 1996

[30] Foreign Application Priority Data

Oct. 23, 1995 [DE] Germany .................. 195 39 293.0

[51] Int. Cl.$^6$ ................................. C07C 255/27
[52] U.S. Cl. ........................................... 558/443
[58] Field of Search ............................... 558/443

[56] References Cited

U.S. PATENT DOCUMENTS 2,553,065  5/1951  Somogyi et al. .............. 260/465.4
5,347,032  9/1994  Reichelt et al. ................ 558/443

FOREIGN PATENT DOCUMENTS 0 583 694  2/1994  European Pat. Off. .
127 117    9/1977  Germany .

OTHER PUBLICATIONS

Ulmann's Encyclopedia of Industrial Chemistry, Fifth Edition, vol. A10: Ethanolamines to Fibers, 4. Synthetic Organic, pp. 284–285 (1980).

Ulmann's Encyclopedia of Industrial Chemistry, Fifth Edition, vol. A1, pp. 290–293 (1982).

*Primary Examiner*—Robert W. Ramsher
*Assistant Examiner*—Ebenezer Sackey
*Attorney, Agent, or Firm*—Oblon, Spivak, McClelland, Maier & Neustadt, P.C.

[57] ABSTRACT

A process for preparing alkyl cyanoacetates of the general formula I

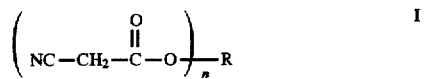

where R is an n-valent aliphatic radical which has 6 to 20 carbon atoms and whose carbon framework can be interrupted by one to three oxygen atoms in ether functionality, and n is a number from 1 to 6, by reacting cyanoacetic acid in aqueous medium with an alcohol $R(OH)_n$, where the esterification is carried out in the presence of an inert entrainer and, during the reaction, water and entrainer are distilled out.

8 Claims, No Drawings

PREPARATION OF ALKYL CYANOACETATES

The present invention relates to a process for preparing cyanoacetic esters of the general formula I

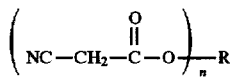

where R is an n-valent aliphatic radical which has 6 to 20 carbon atoms and whose carbon framework can be interrupted by one to three oxygen atoms in ether functionality, and n is a number from 1 to 6, by reacting cyanoacetic acid in aqueous medium with an alcohol $R(OH)_n$.

Cyanoacetic acid is generally prepared by reacting chloroacetic acid with cyanide salts. This reaction results in aqueous crude product solutions which generally have a cyanoacetic acid content of from 20 to 80% of the total weight of the crude product solution. There has therefore been a search for processes for esterifying cyanoacetic acid which make it possible to esterify cyanoacetic acid in aqueous medium without elaborate purification steps.

DE-A 4227505 describes a process for preparing $C_4$–$C_{10}$-alkyl cyanoacetates by reacting cyanoacetic acid with $C_4$–$C_{10}$-alcohols, where cyanoacetic acid is reacted in aqueous medium with a 5- to 30-fold molar excess of a $C_4$–$C_{10}$-alcohol and, during this, the $C_4$–$C_{10}$-alcohol/water azeotrope is distilled out.

However, the products obtained in this way often, especially on esterification with higher alcohols, are discolored and contain unwanted by-products such as dialkyl malonates. An additional disadvantage is the large amount of alcohol required for the azeotropic esterification.

It is an object of the present invention to find a process for preparing cyanoacetic esters I from aqueous medium which avoids these disadvantages and leads to purer products.

We have found that this object is achieved by a process for preparing alkyl cyanoacetates of the general formula I

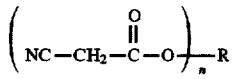

where R is an n-valent aliphatic radical which has 6 to 20 carbon atoms and whose carbon framework can be interrupted by one to three oxygen atoms in ether functionality, and n is a number from 1 to 6, by reacting cyanoacetic acid in aqueous medium with an alcohol $R(OH)_n$, wherein the esterification is carried out in the presence of an inert entrainer and, during the reaction, water and entrainer are distilled out under atmospheric or reduced pressure.

The process according to the invention involves esterification of cyanoacetic acid in aqueous medium. As a rule, this starts from an aqueous cyanoacetic acid solution which has a cyanoacetic acid content of 20–80%, preferably 60–70%, of the weight of the solution.

It is particularly advantageous to react an aqueous mixture of haloacetic acid and alkali metal cyanide in situ with the appropriate alcohol, ie. without previous purification of the resulting cyanoacetic acid.

The aliphatic radical R in the alcohols $R(OH)_n$ used is, for example, a branched or unbranched alkyl group having 6 to 20 carbon atoms.

It is particularly preferred to use monohydric alcohols which contain, for example, the radicals hexyl, 2-methylpentyl, heptyl, 2-methylhexyl, octyl, isooctyl, 2-ethylhexyl, nonyl, 2-methylnonyl, isononyl, 2-methyloctyl, decyl, isodecyl, 2-methylnonyl, undecyl, isoundecyl, dodecyl, isododecyl, tridecyl, isotridecyl, tetradecyl, pentadecyl, hexadecyl, heptadecyl, octadecyl, nonadecyl or eicosyl. (The names isooctyl, isononyl, isodecyl and isotridecyl are trivial names derived from the carbonyl compounds obtained in the oxo synthesis; cf. in this connection Ullmann's Encyclopedia of Industrial Chemistry, 5th Edition, Vol. A1, pages 290–293, and Vol. A10, pages 284 and 285).

Among these alcohols, those having 6 to 13 carbon atoms are preferred.

2-Ethylhexanol is particularly preferably used for the esterification.

When n=2 to 6, suitable examples of n-valent radicals R derived from polyols of the formula $R(OH)_n$ are, in particular, those having 2 to 12 carbon atoms which can be interrupted in their linear or branched carbon framework by up to 3 oxygen atoms in ether functionality. Specific examples thereof are:

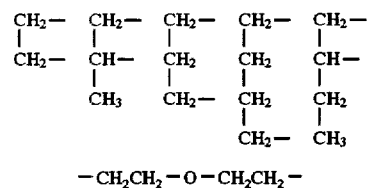

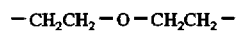

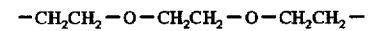

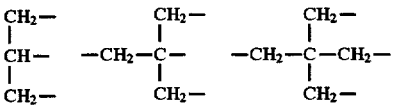

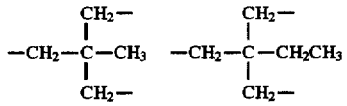

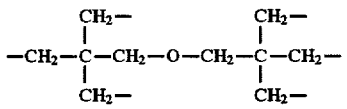

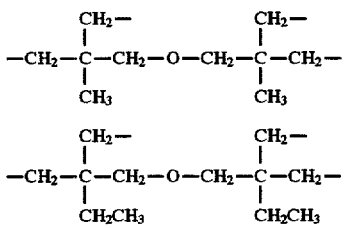

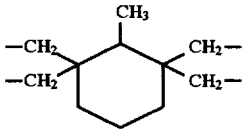

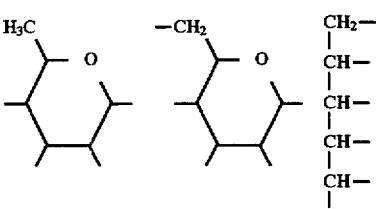

The preferred molar ratio between cyanoacetic acid and alcohol component depends on the number of hydroxyl groups in the latter. In general, from 0.5 to 2 mol, preferably 0.8 to 1.2 mol, particularly preferably about 1 mol, of cyanoacetic acid is used per mole of free hydroxyl groups.

The process according to the invention can be carried out under atmospheric pressure or, advantageously, under reduced pressure, with a pressure of from 200 to 400 mbar being particularly favorable.

The reaction temperature essentially depends on the pressure, because the boiling point of the mixture of water and entrainer is determined by the pressure. In general, the reaction is carried out at from 50° to 150° C., preferably 70° to 130° C., particularly preferably 90° to 110° C.

Various inert solvents can be used as entrainers. The choice thereof depends, for example, on the availability and the boiling point. The azeotrope of water and entrainer should have a lower boiling point than the alcohol used. Examples of suitable inert entrainers are toluene, xylene, heptane, cyclohexane and methyl-cyclohexane. Toluene is particularly preferably used.

In a preferred embodiment, the entrainer is separated from the water after the distilling out and is returned to the reaction vessel. This means that only a relatively small amount of entrainer is required. The amount of entrainer preferably added to the reaction mixture is from 30 to 300%, particularly preferably from 50 to 200%, of the weight of the water present in the reaction mixture.

It is advantageous for the reaction according to the invention to add a catalyst. Suitable catalysts are basic compounds such as carbonates, but in particular acids.

Particularly suitable acids are strong to moderately strong inorganic or organic acids, such as sulfuric acid, hydrochloric acid, phosphoric acid, benzenesulfonic acid, o- or p-toluenesulfonic acid, methanesulfonic acid, trifluoromethanesulfonic acid, trifluoroacetic acid or mono-, di- or trichloroacetic acid. The use of sulfuric acid or p-toluenesulfonic acid is preferred, and the use of sulfuric acid should be particularly emphasized.

Catalytic amounts normally mean from 0.001 to 0.01 mol of acid per 1 mol of cyanoacetic acid, it also being possible to use larger amounts of mineral acids, eg. 0.01 to 0.1 mol.

The process according to the invention can be carried out either continuously or batchwise.

The end of the reaction can easily be recognized from the fact that the distillate no longer contains water. In a preferred embodiment of the invention, the pressure is then reduced further, eg. to 10 to 50 mbar, and the remainder of the entrainer is distilled out under this. The mixture is then cooled and, after addition of water, neutralized, and the organic phase is separated from the aqueous phase.

It is also possible as an alternative for the entrainer to be distilled out under reduced pressure after the phase separation.

The process according to the invention results in alkyl cyanoacetates of high purity and very little color. The small amount of dialkyl malonate in the product is a particular advantage. The alkyl cyanoacetates prepared according to the invention are important precursors for light stabilizers.

EXAMPLE 912 g (7.5 mol) of 70% by weight aqueous cyanoacetic acid solution were mixed with 350 ml of toluene and 974 g (7.5 mol) of 2-ethylhexanol, and 30 ml of 96% by weight sulfuric acid. The pressure in the reaction vessel was reduced to 300 mbar and subsequently, at an internal temperature of 100° C., the toluene/water mixture was distilled out, returning the toluene which had separated out to the reaction vessel. After the esterification was complete, the toluene was completely distilled out under 25 mbar, and then the mixture was cooled to 40° C. and 280 ml of water were added. The pH was adjusted to 7 by adding 50% by weight NaOH, and the organic phase was separated off. Yield: 88%

We claim:

1. A process for preparing alkyl cyanoacetates of the general formula I

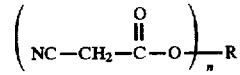

wherein R is an n-valent aliphatic radical which has 6 to 20 carbon atoms and whose carbon framework can be interrupted by one to three oxygen atoms in ether functionality, and n is a number from 1 to 6, by reacting cyanoacetic acid in aqueous medium with an alcohol $R(OH)_n$, wherein the esterification is carried out in the presence of an inert entrainer other than water, and, during the reaction, water and entrainer are distilled out under atmospheric or reduced pressure.

2. A process as claimed in claim 1, wherein n is 1.

3. A process as claimed in claim 1, wherein R is an aliphatic radical having 6 to 13 carbon atoms.

4. A process as claimed in claim 1, wherein R is 2-ethylhexyl.

5. A process as claimed in claim 1, wherein the reaction is carried out at from 70° to 130° C.

6. A process as claimed in claim 1, wherein the reaction is carried out under a pressure of from 200 to 400 mbar.

7. A process as claimed in claim 1, wherein toluene, xylene, heptane, cyclohexane or methylcyclohexane is used as inert entrainer.

8. A process as claimed in claim 7, wherein toluene is used as inert entrainer.

* * * * *